United States Patent

Kopkalli et al.

(10) Patent No.: US 8,859,829 B2
(45) Date of Patent: Oct. 14, 2014

(54) STABILIZER AND INHIBITOR FOR CHLOROPROPENES, SUCH AS TETRACHLOROPROPENE 1,1,2,3-TETRACHLOROPROPENE (1230XA), USED IN THE MANUFACTURE OF 2,3,3,3-TETRAFLUOROPROPENE (1234YF)

(71) Applicant: Honeywell International Inc., Morristown, NJ (US)

(72) Inventors: Haluk Kopkalli, Staten Island, NY (US); Haiyou Wang, Amherst, NY (US); Hsueh Sung Tung, Getzville, NY (US); Daniel C. Merkel, Orchard Park, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 14/203,714

(22) Filed: Mar. 11, 2014

(65) Prior Publication Data

US 2014/0275650 A1      Sep. 18, 2014

Related U.S. Application Data

(60) Provisional application No. 61/782,117, filed on Mar. 14, 2013.

(51) Int. Cl.
| | | |
|---|---|---|
| *C07C 17/20* | (2006.01) | |
| *C07C 17/00* | (2006.01) | |
| *C09K 15/32* | (2006.01) | |
| *C09K 15/16* | (2006.01) | |
| *C09K 15/06* | (2006.01) | |
| *C07C 17/42* | (2006.01) | |

(52) U.S. Cl.
CPC ............... *C07C 17/202* (2013.01); *C07C 17/42* (2013.01)
USPC ........... 570/160; 570/156; 570/161; 570/163; 252/400.2; 252/405; 252/407; 422/430

(58) Field of Classification Search
USPC ............... 570/160, 156, 163, 161; 252/400.2, 252/405, 407; 422/430
See application file for complete search history.

(56) References Cited

U.S. PATENT DOCUMENTS

| | | | |
|---|---|---|---|
| 2,721,883 A | 10/1955 | Stevens | |
| 2,931,840 A | 4/1960 | Marquis et al. | |
| 4,416,797 A * | 11/1983 | Minagawa et al. | ........ 252/400.1 |
| 4,900,874 A | 2/1990 | Ihara et al. | |
| 5,162,594 A | 11/1992 | Krespan | |
| 6,350,395 B1 | 2/2002 | Kuemin | |
| 6,534,688 B2 | 3/2003 | Klausmeyer | |
| 7,795,480 B2 | 9/2010 | Merkel et al. | |
| 2009/0240090 A1 | 9/2009 | Merkel et al. | |
| 2011/0130599 A1 | 6/2011 | Elsheikh et al. | |
| 2011/0196178 A1 | 8/2011 | Nyberg | |
| 2012/0136182 A1 | 5/2012 | Merkel et al. | |
| 2012/0190902 A1* | 7/2012 | Nyberg | ......................... 570/160 |
| 2012/0226081 A1 | 9/2012 | Elsheikh | |

FOREIGN PATENT DOCUMENTS

| | | |
|---|---|---|
| EP | 0309958 A2 | 9/1988 |
| JP | 2012046462 A | 3/2012 |
| WO | WO02100809 A2 | 12/2002 |
| WO | WO2009003165 A1 | 12/2008 |

OTHER PUBLICATIONS

Banks, et al., Journal of Fluorine Chemistry, vol. 82, Iss. 2, p. 171-174 (1997).

* cited by examiner

*Primary Examiner* — Jafar Parsa
(74) *Attorney, Agent, or Firm* — Scully, Scott, Murphy & Presser, P.C.

(57) ABSTRACT

The present invention relates in part to a method of stabilizing chloropropenes, such as 1,1,2,3-tetrachloropropene, otherwise known to decompose and degrade, and to the resulting stabilized chloropropene, using a morpholine compound and/or a trialkyl phosphate compound as defined herein. Such stabilized chloropropenes are useful in the manufacture of hydrofluoroolefins such as 2,3,3,3-tetrafluoroprop-1-ene (1234yf).

31 Claims, No Drawings

STABILIZER AND INHIBITOR FOR CHLOROPROPENES, SUCH AS TETRACHLOROPROPENE 1,1,2,3-TETRACHLOROPROPENE (1230XA), USED IN THE MANUFACTURE OF 2,3,3,3-TETRAFLUOROPROPENE (1234YF)

FIELD OF THE INVENTION

The present invention relates to the stabilization of chloropropenes, including tetrachloropropenes, such as 1,1,2,3-tetrachloropropene (TCP or 1230xa).

BACKGROUND OF THE INVENTION

Hydrofluoroolefins (HFOs), such as tetrafluoropropenes (including 2,3,3,3-tetrafluoropropene (HFO-1234yf)), are now known to be effective refrigerants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike chlorofluorocarbons (CFCs) and hydrochlorofluorocarbons (HCFCs), both of which potentially damage the Earth's ozone layer, HFOs do not contain chlorine and, thus, pose no threat to the ozone layer. HFO-1234yf has been shown to be a low global warming compound with low toxicity and, hence, can meet increasingly stringent requirements for refrigerants in mobile air conditioning. It has been found to be an effective refrigerant, heat transfer medium, propellant, foaming agent, blowing agent, gaseous dielectric, sterilant carrier, polymerization medium, particulate removal fluid, carrier fluid, buffing abrasive agent, displacement drying agent and power cycle working fluid. Accordingly, compositions containing HFO-1234yf are among the materials being developed for use in many of the aforementioned applications. Thus, there is a need for new manufacturing processes for the production of tetrafluoropropenes and in particular 2,3,3,3-tetrafluoropropene.

Several methods of preparing HFOs are known. For example, U.S. Pat. No. 4,900,874 (Ihara et al.) describes a method of making fluorine containing olefins by contacting hydrogen gas with fluorinated alcohols. Although this appears to be a relatively high-yield process, commercial scale handling of hydrogen gas at high temperature is hazardous. Also, the cost of commercially producing hydrogen gas, such as building an on-site hydrogen plant, is economically costly.

U.S. Pat. No. 2,931,840 (Marquis) describes a method of making fluorine containing olefins by pyrolysis of methyl chloride and tetrafluoroethylene or chlorodifluoromethane. This process is a relatively low yield process, and a very large percentage of the organic starting material is converted to unwanted and/or unimportant byproducts, including a sizeable amount of carbon black which tends to deactivate the catalyst used in the process.

The preparation of HFO-1234yf from trifluoroacetylacetone and sulfur tetrafluoride has been described (See Banks, et al., Journal of Fluorine Chemistry, Vol. 82, Iss. 2, p. 171-174 (1997)). Also, U.S. Pat. No. 5,162,594 (Krespan) discloses a process wherein tetrafluoroethylene is reacted with another fluorinated ethylene in the liquid phase to produce a polyfluoroolefin product.

Manufacturing processes for HFO-1234yf, as disclosed e.g. in U.S. Pat. No. 8,058,486, use among other things, chloropropenes such as 1,1,2,3-tetrachloropropene (HCO-1230xa) as a starting raw material. In one practice, the process consists of the following three steps:

1) HCO-1230xa+3HF→2-chloro-3,3,3-trifluoropropene (HCFO-1233xf)+3HCl in a vapor phase reactor charged with a solid hydrofluorination catalyst such as fluorinated chromia,
2) HCFO-1233xf+HF→2-chloro-1,1,1,2-tetrafluoropropane (HCFC-244bb) in a liquid phase reactor charged with a liquid hydrofluorination catalyst such as fluorinated $SbCl_5$, and
3) HCFC-244bb→HFO-1234yf+HCl in a vapor phase reactor.

During storage and transport of chloropropenes, such as 1,1,2,3-tetrachloropropene (1230xa), it has been found that decomposition and/or other forms of degradation can occur. This can result in the formation of undesirable components such as acids, e.g., HCl, and also oxidation by-products, oligomers, and the like. Formation of these is exacerbated when the chloropropene is in contact with metal, including the metal containers used for storage and transport. Among other things, these decomposition products can adversely affect the first step (Step 1, whereby 1233xf is produced) of the aforementioned three-step process to produce 1234yf.

Thus there is a need to stabilize reagents such as chloropropenes, and inhibit the formation of these decomposition products.

SUMMARY OF THE INVENTION

The present invention relates, in part, to a method of stabilizing a chloropropene; a stabilized composition comprising a chloropropene; the use of a stabilized chloropropene in preparing 2-chloro-3,3,3-trifluoropropene (1233xf), and in preparing 2,3,3,3-tetrafluoroprop-1-ene (1234yf).

Without limitation: in one aspect, the present invention is a method for stabilizing a chloropropene comprising (a) providing a chloropropene, and (b) adding to said chloropropene a stabilizingly effective amount of at least one stabilizer compound selected from (i) or (ii) and combinations thereof:
(i) a morpholine compound having the formula:

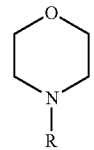

wherein R is H or a $C_1$-$C_6$ alkyl, or (ii) a trialkyl phosphate compound having the formula $R'_3PO_4$, wherein R' is a $C_1$-$C_6$ alkyl. Combinations of stabilizer compounds having formulas (i) and (ii) may also be employed.

Another aspect the invention is directed to a composition comprising a chloropropene and at least one stabilizer compound having the aforesaid formulas. In still another aspect the invention is directed to an article of manufacture, such as a container, including storage and shipping containers for choloropenes, within which comprises the stabilized composition of the invention. Yet another aspect of the invention is a method of preparing 2-chloro-3,3,3-trifluoropropene (1233xf), and separately, of preparing 2,3,3,3-tetrafluoroprop-1-ene (1234yf) using the stabilized chloropropene as described herein. In addition to stabilizing chloropropenes, the present invention also inhibits decomposition, retards corrosion, and scavenges acids, all of which, among other things, improve processes to prepare 2-chloro-3,3,3-trifluoropropene (1233xf) and 2,3,3,3-tetrafluoroprop-1-ene (1234yf).

DETAILED DESCRIPTION OF THE INVENTION

The foregoing general description and the following detailed description are exemplary and explanatory only and are not restrictive of the invention, as defined in the appended claims. Other features and benefits of any one or more of the embodiments will be apparent from the following detailed description, and from the claims. The entire contents of each of U.S. Pat. No. 8,084,653 and of US Published Patent Application 2009/0240090 are incorporated herein by reference.

In a first embodiment, the present invention relates to a method for stabilizing a chloropropene, which method comprises (a) providing a chloropropene; and (b) adding to said chloropropene a stabilizingly effective amount of at least one stabilizer compound selected from (i) or (ii) and combinations thereof: (i) a morpholine compound having the formula:

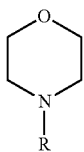

wherein R is hydrogen (H) or a $C_1$-$C_6$ alkyl, (ii) a trialkyl phosphate compound having the formula $R'_3PO_4$, wherein R' is a $C_1$-$C_6$ alkyl.

Without limitation, in one practice, chloropropenes include chloropropenes having three carbon atoms, including, for example, tetrachloropropenes, such as 1,1,2,3-tetrachloropropene, 2,3,3,3-tetrachloropropene, 1,1,3,3-tetrachloropropene, 1,3,3,3-tetrachloropropene, 1,2,3,3-tetrachloropropene; trichloropropenes, such as 1,1,3-trichloropropene; combinations of various chloropropenes, including the foregoing, are encompassed by the term, as are all cis and trans configurations of same. In one embodiment, the chloropropene is a tetrachloropropene; in another embodiment it is 1,1,2,3-tetrachloropropene (1230xa or TCP). In another embodiment, the chloropropene subject of the invention includes one or more chlorinated compounds selected from Formula I or II or combinations of same:

wherein X is independently selected from fluorine (F), chlorine (Cl), bromine (Br) and iodine (I), provided that at least one of X is not F.

In another aspect, the morpholine compound has the generic formula (i) above, wherein R is H or a $C_1$-$C_6$ alkyl (e.g. $C_1$, $C_2$, $C_3$, $C_4$, $C_5$, $C_6$ alkyl and combinations and permutations of any thereof). In one embodiment, R is a $C_1$-$C_3$ alkyl. In another embodiment, R is a $C_1$ alkyl(methyl). In another aspect, the trialkyl phosphate compound has the generic formula (ii) above, wherein R' is a $C_1$-$C_6$ alkyl (e.g. $C_1$, $C_2$, $C_3$, $C_4$, $C_5$, $C_6$ alkyl and combinations and permutations of any thereof). In one embodiment, R' is a $C_2$-$C_4$ alkyl. In another embodiment, R' is a $C_4$ alkyl(butyl). In certain embodiments, the trialkyl phosphate compound of formula (ii) is tributyl phosphate (TBP), and/or tripropyl phosphate (TPP) and/or triethyl phosphate (TEP). The term "alkyl" as used herein includes cyclic or acyclic and straight-chain or branched alkyl groups, such as, methyl, ethyl, n-propyl, i-propyl, or the different isomers thereof. In certain embodiments, R and R' are each independently a straight-chain or branched alkyl. In certain other embodiments of the morpholine compound, R is H (i.e., the morpholine compound is "morpholine"). The stabilizer compound can be added to the chloropropene by methods known in the art.

In one practice, no other stabilizers or inhibitors are present in the chloropropene other than the morpholine compound (i) and/or the trialkyl phosphate compound (ii); in one practice, no other stabilizers or inhibitors are present in the chloropropene other than the morpholine compound (i); in another practice, no other stabilizers or inhibitors are present in the chloropropene other than the trialkyl phosphate compound (ii); such other stabilizers or inhibitors include, without limitation, e.g., compounds such as amines, including straight and cyclic amines and primary amines, phenols, oxides, quinones, hydroquinones such as monomethyl ether hydroquinone (MEHQ), styrenes, and the like; alternatively, if such other stabilizers or inhibitors are present in the practice of the invention, they are present in non-stabilizingly effective amounts. In another practice, the invention, as described in its various embodiments herein, and in the context of stabilizers, consists essentially of the morpholine compound (i) or the trialkyl phosphate compound (ii) as stabilizer; in another practice, the invention, as described in its various embodiments herein, it consists of the morpholine compound (i) or the trialkyl phosphate compound (ii) as stabilizer. In a particular practice, the stabilizer compound is morpholine only (R is H).

The phrase "stabilizingly effective amount" intends an amount of stabilizer compound that either prevents decomposition and/or other forms of degradation in the chloropropene, including the formation of undesirable components such as acids, e.g., HCl, oxidation by-products, oligomers, and the like; or inhibits such decomposition to a point whereby such undesirable components are present in amounts immaterial to further processing, e.g., they do not need to be removed or they do not have any meaningful effect on operations or processing, e.g. in processes to prepare 2-chloro-3,3,3-trifluoropropene (1233xf) and/or 2,3,3,3-tetrafluoroprop-1-ene (1234yf). In one embodiment, a stabilizingly effective amount is about 5 ppm to about 1000 ppm stabilizer compound by weight chloropropene. In another embodiment, a stabilizingly effective amount is about 100 ppm to about 800 ppm stabilizer compound by weight chloropropene. In still another embodiment, a stabilizingly effective amount is about 200 ppm to about 500 ppm stabilizer compound by weight chloropropene. It will be understood to the artisan that the ppm ranges given herein include all ppm's between said ranges, whether integer or fractional, and includes endpoints; thus about 5 ppm to about 1000 ppm includes, 6 ppm, 7 ppm . . . 998 ppm, 999 ppm, and the like, including ppm amounts in between and endpoints.

In other embodiment, the present invention relates to a composition comprising a chloropropene and at least one stabilizer compound, all as defined herein. In one practice, the stabilizer compound is present in a stabilizingly effective amount. In one aspect, the stabilizer compound is present in an amount from about 5 ppm to about 1000 ppm. In another practice, for the morpholine compound of formula (i), R is H or $C_1$-$C_6$ alkyl; in another practice, R is H or $C_1$-$C_3$ alkyl; in another practice, R is $C_1$ alkyl; in another practice, R is H, i.e. the morpholine compound is morpholine per se. In another practice, for the trialkyl phosphate compound of formula (ii), R' is $C_1$-$C_6$ alkyl; in another R' is $C_2$-$C_4$ alkyl; in yet another, R' is $C_4$ alkyl.

In another embodiment the present invention relates to an article of manufacture comprising such a stabilized compound. In one practice, the article of manufacture is a container, such as a container used for transporting or storing a chloropropene. In another aspect, the container is a metal container. In an embodiment of this practice, the container comprises a metal such as, without limitation, stainless steel, e.g. SS316; Monel alloys e.g. Monel 400; Inconel alloys e.g. Inconel 600 and Inconel 625. Other metals suitable for containing chloropropenes, such as 1,1,2,3-tetrachloropropene (1230xa) are within contemplation of the invention. Articles of manufacture, such as the containers herein, can also be lined with, e.g. fluoropolymers or other suitable materials. In one practice, the stabilizer compound is added in a stabilizingly effective amount to the chloropropene by a choropropene supplier, e.g., prior to shipment.

In another embodiment, the present invention relates to a method for preparing 2-chloro-3,3,3-trifluoropropene (1233xf) comprising (a) providing a starting composition comprising a chloropropene and a stabilizingly effective amount of at least one stabilizer compound as defined herein; and (b) contacting said starting composition with a fluorinating agent under conditions effective to produce a first composition comprising 2-chloro-3,3,3-trifluoropropene. In step (b), the stabilizer compound may be optionally removed, or not, from said starting composition prior to said contacting. The stabilizer compound may be removed by techniques known in the art, including without limitation, by one or more of the following: selective adsorption with a solid adsorbent selected from the group consisting of activated carbons and zeolite molecular sieves; flash removal under vacuum conditions. In another practice, the chloropropene and the stabilizingly effective amount of stabilizer compound is contacted as such that is, the stabilized chloropropene is used as a reactant, as such, in the method to prepare 2-chloro-3,3,3-trifluoropropene (1233xf). The fluorinating agent include those known in the art, e.g., HF, as disclosed herein. Optionally, the starting composition may be contacted with the fluorinating agent in the presence of a fluorination catalyst, e.g. chromium oxide ($Cr_2O_3$) as known in the art, as disclosed herein.

In another embodiment, the invention relates to a method for preparing 2,3,3,3-tetrafluoroprop-1-ene (1234yf) comprising (a) providing a starting composition comprising at least one compound having a structure selected from Formula I or II:

1) $CX_2=CCl-CH_2X$  (Formula I)

2) $CX_3-CCl=CH_2$  (Formula II)

wherein X is independently selected from F, Cl, Br and I, provided that at least one of X is not F, and a stabilizingly effective amount of at least one stabilizer compound as described herein;
(b) contacting said starting composition with a first fluorinating agent to produce a first intermediate composition comprising 2-chloro-3,3,3-trifluoropropene and a first chlorine-containing byproduct, wherein in step (b) said stabilizer compound is optionally removed from said starting composition prior to said contacting; (c) contacting said first intermediate composition with a second fluorinating agent to produce a second intermediate composition comprising 2-chloro-1,1,1,2-tetrafluoropropane; and (d) dehydrochlorinating at least a portion of said 2-chloro-1,1,1,2-tetrafluoropropane to produce a reaction product comprising 2,3,3,3-tetrafluoroprop-1-ene and a second chlorine-containing byproduct.

The method to make 2,3,3,3-tetrafluoroprop-1-ene (1234yf) generally includes at least three reaction steps. In the first step, a starting composition including compounds of chloropropenes Formula I and/or II e.g. 1,1,2,3-tetrachloropropene, 2,3,3,3-tetrachloropropene, is reacted with anhydrous HF in a first vapor phase reactor (fluorination reactor) to produce a mixture of 2-chloro-3,3,3-trifluoropropene (1233xf) and HCl. In certain embodiments, the reaction occurs in the vapor phase in the presence of a vapor phase catalyst, such as, but not limited to, a fluorinated chromium oxide. The catalyst may (or may not) have to be activated with anhydrous hydrogen fluoride (hydrogen fluoride gas) before use depending on the state of the catalyst. Starting compositions having the formula $CX_3-CHCl-CH_2X$ (Formula III), such as 1,1,1,2,3-pentachloropropane may also be used, and the instant invention contemplates mixtures of this Formula III composition with the chloropropenes described herein, including those of Formula I and II, as stabilized, as starting compositions.

While fluorinated chromium oxides are disclosed as the vapor phase catalyst, the present invention is not limited to this embodiment. Any fluorination catalysts known in the art may be used in this process. Suitable catalysts include, but are not limited to chromium, aluminum, cobalt, manganese, nickel and iron oxides, hydroxides, halides, oxyhalides, inorganic salts thereof and their mixtures and any one of which may be optionally fluorinated. Combinations of catalysts suitable for the present invention nonexclusively include $Cr_2O_3$, $FeCl_3/C$, $Cr_2O_3/Al_2O_3$, $Cr_2O_3/AlF_3$, $Cr_2O_3/carbon$, $CoCl_2/Cr_2O_3/Al_2O_3$, $NiCl_2/Cr_2O_3/Al_2O_3$, $CoCl_2/AlF_3$, $NiCl_2/AlF_3$ and mixtures thereof. Chromium oxide/aluminum oxide catalysts are described in U.S. Pat. No. 5,155,082 which is incorporated herein by reference. Chromium (III) oxides such as crystalline chromium oxide or amorphous chromium oxide are preferred with amorphous chromium oxide being most preferred. Chromium oxide ($Cr_2O_3$) is a commercially available material which may be purchased in a variety of particle sizes. Fluorination catalysts having a purity of at least 98% are preferred. The fluorination catalyst is present in an excess but in at least an amount sufficient to drive the reaction.

This first step of the reaction may be conducted in any reactor suitable for a vapor phase fluorination reaction. In certain embodiments, the reactor is constructed from materials which are resistant to the corrosive effects of hydrogen fluoride and catalyst such as Hastalloy, Nickel, Incoloy, Inconel, Monel and fluoropolymer linings. The vessel is a fixed catalyst bed or fluidized bed. If desired, inert gases such as nitrogen or argon may be employed in the reactor during operation.

In general, the effluent from the fluorination reaction step, including any intermediate effluents that may be present in multi-stage reactor arrangements, may be processed to achieve desired degrees of separation and/or other processing. For example, in embodiments in which the reactor effluent includes 1233xf, the effluent will generally also include HCl and one or more of HF, 2,3-dichloro-3,3-difluoropropene (1232xf), 1,2-dichloro-3,3,3-trifluoropropene (1223xd), trichlorofluoropropene (1231) isomers, 2-chloro-1,1,1,2-tetrachloropropane (244bb), and unreacted 1230xa, 1230xf, and/or 240 db. Some portion or substantially all of these components of the reaction product may be recovered from the reaction mixture via any separation or purification method known in the art such as neutralization and distillation. It is expected that unreacted starting materials and HF could be recycled, completely or partially, to improve the overall yield of the desired 1233xf. 1232xf and any 1231 formed may also be recycled.

Optionally, hydrogen chloride is then recovered from the result of the fluorination reaction. Recovering of hydrogen chloride is conducted by conventional distillation where it is removed as the distillate. Alternatively, HCl can be recovered or removed by using water or caustic scrubbers. When a water extractor is used, HCl is removed as an aqueous solution. When caustic scrubbers are used, HCl is just removed from the system as a chloride salt in aqueous solution.

In the second step of the process for forming 2,3,3,3-tetrafluoroprop-1-ene, 1233xf is converted to 2-chloro-1,1,1,2-tetrafluoropropane (244bb). In one embodiment, this step may be performed in the liquid phase in a liquid phase reactor, which may be PTFE or PFA-lined. Such a process may be performed in a temperature range of about 70-120° C. and about 50-120 psig.

Any liquid phase fluorination catalyst may be used in the invention. A non-exhaustive list include Lewis acids, transition metal halides, transition metal oxides, Group IVb metal halides, a Group Vb metal halides, or combinations thereof. Non-exclusive examples of liquid phase fluorination catalysts are an antimony halide, a tin halide, a tantalum halide, a titanium halide, a niobium halide, and molybdenum halide, an iron halide, a fluorinated chrome halide, a fluorinated chrome oxide or combinations thereof. Specific non-exclusive examples of liquid phase fluorination catalysts are $SbCl_5$, $SbCl_3$, $SbF_5$, $SnCl_4$, $TaCl_5$, $TiCl_4$, $NbCl_5$, $MoCl_6$, $FeCl_3$, a fluorinated species of $SbCl_5$, a fluorinated species of $SbCl_3$, a fluorinated species of $SnCl_4$, a fluorinated species of $TaCl_5$, a fluorinated species of $TiCl_4$, a fluorinated species of $NbCl_5$, a fluorinated species of $MoCl_6$, a fluorinated species of $FeCl_3$, or combinations thereof. Antimony pentachloride is most preferred.

These catalysts can be readily regenerated by any means known in the art if they become deactivated. One suitable method of regenerating the catalyst involves flowing a stream of chlorine through the catalyst. For example, from about 0.002 to about 0.2 lb per hour of chlorine can be added to the liquid phase reaction for every pound of liquid phase fluorination catalyst. This may be done, for example, for from about 1 to about 2 hours or continuously at a temperature of from about 65° C. to about 100° C.

This second step of the reaction is not necessarily limited to a liquid phase reaction and may also be performed using a vapor phase reaction or a combination of liquid and vapor phases, such as that disclosed in U.S. Published Patent Application No. 20070197842, the contents of which are incorporated herein by reference. To this end, the 1233xf containing feed stream is preheated to a temperature of from about 50° C. to about 400° C., and is contacted with a catalyst and fluorinating agent. Catalysts may include standard vapor phase agents used for such a reaction and fluorinating agents may include those generally known in the art, such as, but not limited to, hydrogen fluoride.

In the third step of 1234yf production, the 244bb is fed to a second vapor phase reactor (dehydrochlorination reactor) to be dehydrochlorinated to make the desired product 2,3,3,3-tetrafluoroprop-1-ene (1234yf). This reactor contains a catalyst that can catalytically dehydrochlorinate HCFC-244bb to make HFO-1234yf.

The catalysts may be metal halides, halogenated metal oxides, neutral (or zero oxidation state) metal or metal alloy, or activated carbon in bulk or supported form. Metal halide or metal oxide catalysts may include, but are not limited to, mono-, bi-, and tri-valent metal halides, oxides and their mixtures/combinations, and more preferably mono-, and bi-valent metal halides and their mixtures/combinations. Component metals include, but are not limited to, $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$. Component halogens include, but are not limited to, $F^-$, $Cl^-$, $Br^-$, and $I^-$. Examples of useful mono- or bi-valent metal halide include, but are not limited to, LiF, NaF, KF, CsF, $MgF_2$, $CaF_2$, LiCl, NaCl, KCl, and CsCl. Halogenation treatments can include any of those known in the prior art, particularly those that employ HF, $F_2$, HCl, $Cl_2$, HBr, $Br_2$, HI, and $I_2$ as the halogenation source.

When neutral, i.e., zero valent, metals, metal alloys and their mixtures are used. Useful metals include, but are not limited to, Pd, Pt, Rh, Fe, Co, Ni, Cu, Mo, Cr, Mn, and combinations of the foregoing as alloys or mixtures. The catalyst may be supported or unsupported. Useful examples of metal alloys include, but are not limited to, SS 316, Monel 400, Inconel 825, Inconel 600, and Inconel 625.

Preferred, but non-limiting, catalysts include activated carbon, stainless steel (e.g. SS 316), austenitic nickel-based alloys (e.g. Inconel 625), nickel, fluorinated 10% CsCl/MgO, and 10% $CsCl/MgF_2$. The reaction temperature is preferably about 300-550° C. and the reaction pressure may be between about 0-150 psig. The reactor effluent may be fed to a caustic scrubber or to a distillation column to remove the by-product of HCl to produce an acid-free organic product which, optionally, may undergo further purification using one or any combination of purification techniques that are known in the art.

What is claimed is:

1. A method for stabilizing a chloropropene comprising:
   (a) providing a chloropropene; and
   (b) adding to said chloropropene a stabilizingl$_y$ effective amount of at least one stabilizer compound selected from (i) or (ii) and combinations thereof:
   (i) a morpholine compound having the formula:

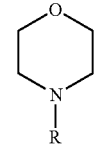

wherein R is H or a $C_1$-$C_6$ alkyl,
   (ii) a trialkyl phosphate compound having the formula $R'_3PO_4$,
   wherein R' is a $C_1$-$C_6$ alkyl.

2. The method of claim 1 wherein said chloropropene is a tetrachloropropene.

3. The method of claim 2 wherein said tetrachloropropene is 1,1,2,3-tetrachloropropene.

4. The method of claim 1 wherein R is H or a $C_1$-$C_3$ alkyl.

5. The method of claim 4 wherein R is $C_1$ alkyl or H.

6. The method of claim 1 wherein R' is a $C_2$-$C_4$ alkyl.

7. The method of claim 6 wherein R' is a $C_4$ alkyl.

8. The method of claim 1 wherein said stabilizer compound is added in an amount of about 5 ppm to about 1000 ppm by weight of said chloropropene.

9. A composition comprising a chloropropene and at least one stabilizer compound selected from (i) or (ii) and combinations thereof:
(i) a morpholine compound having the formula:

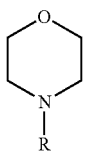

wherein R is H or $C_1$-$C_6$ alkyl,
(ii) a trialkyl phosphate compound having the formula $R'_3PO_4$,
wherein R' is a $C_1$-$C_6$ alkyl.

10. The composition of claim 9 wherein said stabilizer compound is present in a stabilizingly effective amount.

11. The composition of claim 10 wherein said stabilizer compound is present in said composition in an amount of about 5 ppm to about 1000 ppm by weight of said chloropropene.

12. The composition of claim 9 wherein said chloropropene is a tetrachloropropene.

13. The composition of claim 9 wherein said tetrachloropropene is 1,1,2,3-tetrachloropropene.

14. The composition of claim 9 wherein R is H or $C_1$-$C_3$ alkyl.

15. The composition of claim 14 wherein R is $C_1$ alkyl or H.

16. The composition of claim 9 wherein R' is a $C_2$-$C_4$ alkyl.

17. The composition of claim 16 wherein R' is a $C_4$ alkyl.

18. A container within which comprises the composition of claim 9.

19. The container of claim 18 wherein the container comprises stainless steel.

20. A method for preparing 2-chloro-3,3,3-trifluoropropene (1233xf) comprising:
(a) providing a starting composition comprising a chloropropene and a stabilizingly effective amount of at least one stabilizer compound selected from (i) or (ii) and combinations thereof:
(i) a morpholine compound having the formula:

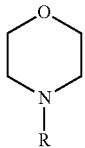

wherein R is H or $C_1$-$C_6$ alkyl,
(ii) a trialkyl phosphate compound having the formula $R'_3PO_4$,
wherein R' is a $C_1$-$C_6$ alkyl;
(b) contacting said starting composition with a fluorinating agent under conditions effective to produce a first composition comprising 2-chloro-3,3,3-trifluoropropene, wherein in step (b) said stabilizer compound is optionally removed from said starting composition prior to said contacting.

21. The method of claim 20 said chloropropene is a tetrachloropropene.

22. The method of claim 21 wherein said tetrachloropropene is 1,1,2,3-tetrachloropropene.

23. The method of claim 20 wherein R is H or a $C_1$-$C_3$ alkyl.

24. The method of claim 23 wherein R is H.

25. The method of claim 20 wherein R' is a $C_2$-$C_4$ alkyl.

26. The method of claim 25 wherein R' is a $C_4$ alkyl.

27. The method of claim 20 wherein said stabilizer compound is present in said first composition in an amount of about 5 ppm to about 1000 ppm by weight of said chloropropene.

28. The method of claim 20 wherein said stabilizer compound is optionally removed by one or more of the following: selective adsorption with a solid adsorbent selected from the group consisting of activated carbons and zeolite molecular sieves, and flash removal under vacuum.

29. The method of claim 20 wherein said fluorinating agent is HF.

30. The method of claim 20 wherein said contacting occurs in the presence of a fluorination catalyst.

31. A method for preparing 2,3,3,3-tetrafluoroprop-1-ene (1234yf) comprising:
a) providing a starting composition comprising at least one compound having a structure selected from Formula I and II:

$$CX_2=CCl-CH_2X \quad \text{(Formula I)}$$

$$CX_3-CCl=CH_2 \quad \text{(Formula II)}$$

wherein X is independently selected from F, Cl, Br and I, provided that at least one of X is not F, and a stabilizingly effective amount of at least one stabilizer compound selected from (i) or (ii) and combinations thereof:
(i) a morpholine compound having the formula:

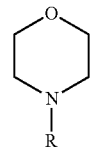

wherein R is H or $C_1$-$C_6$ alkyl,
(ii) a trialkyl phosphate compound having the formula $R'_3PO_4$,
wherein R' is a $C_1$-$C_6$ alkyl;
b) contacting said starting composition with a first fluorinating agent to produce a first intermediate composition comprising 2-chloro-3,3,3-trifluoropropene and a first chlorine-containing byproduct, wherein in step (b) said stabilizer compound is optionally removed from said starting composition prior to said contacting;
c) contacting said first intermediate composition with a second fluorinating agent to produce a second intermediate composition comprising 2-chloro-1,1,1,2-tetrafluoropropane; and
d) dehydrochlorinating at least a portion of said 2-chloro-1,1,1,2-tetrafluoropropane to produce a reaction product comprising 2,3,3,3-tetrafluoroprop-1-ene and a second chlorine-containing byproduct.

* * * * *